US008958611B2

(12) United States Patent
Ikits (10) Patent No.: US 8,958,611 B2
(45) Date of Patent: Feb. 17, 2015

(54) INTERACTIVE CSG SUBTRACTION

(75) Inventor: Milan Ikits, Plantation, FL (US)

(73) Assignee: Mako Surgical Corporation, Fort Lauderdale, FL (US)

( * ) Notice: Subject to any disclaimer, the term of this patent is extended or adjusted under 35 U.S.C. 154(b) by 436 days.

(21) Appl. No.: 13/339,907

(22) Filed: Dec. 29, 2011

(65) Prior Publication Data

US 2013/0172904 A1    Jul. 4, 2013

(51) Int. Cl.
*G06K 9/00* (2006.01)

(52) U.S. Cl.
USPC .......................................... 382/128; 345/630

(58) Field of Classification Search
CPC .............................. G06T 15/005; G06T 17/20
USPC ........... 345/418, 420; 382/131; 600/424, 476; 703/1, 2; 704/205
See application file for complete search history.

(56) References Cited

U.S. PATENT DOCUMENTS

| 6,191,787 | B1* | 2/2001 | Lu et al. ........................ 345/418 |
| 7,092,859 | B2* | 8/2006 | Wang et al. ....................... 703/2 |
| 8,010,180 | B2* | 8/2011 | Quaid et al. ................... 600/424 |
| 8,244,524 | B2* | 8/2012 | Shirakawa et al. ............ 704/205 |
| 8,370,115 | B2* | 2/2013 | Rossignac ........................ 703/1 |
| 8,428,326 | B2* | 4/2013 | Falk et al. ..................... 382/131 |
| 8,483,858 | B2* | 7/2013 | Sullivan et al. ................. 700/97 |
| 2009/0160855 | A1* | 6/2009 | Wu ................................ 345/420 |
| 2010/0256504 | A1* | 10/2010 | Moreau-Gaudry et al. .. 600/476 |
| 2012/0221300 | A1* | 8/2012 | Tukora ............................. 703/1 |
| 2013/0185028 | A1* | 7/2013 | Sullivan ........................... 703/2 |

OTHER PUBLICATIONS

Zhao, H., et al., "Parallel and efficient Boolean on polygonal solids," The Visual Computer, vol. 27, pp. 507-517, Apr. 2011.*

* cited by examiner

*Primary Examiner* — Vikkram Bali
*Assistant Examiner* — Xuemei Chen
(74) *Attorney, Agent, or Firm* — Miller, Matthias & Hull LLP (57) ABSTRACT

A system and method for surgical visualization transform a cut procedure into a visual representation, e.g., during resection via a cutting tool. The system and method obtain shape data, e.g., bone shape data for the bone to be resected, and generate a CSG object model such as a bone model. Another CSG model is also generated, based, for example, on the cutting tool shape. During resection, tool position data is collected and multiple CSG subtraction models are generated based on the cutting tool model and the position data. The CSG bone model and subtraction models are used to create an image space visual representation by merging the CSG subtraction models into a single merged CSG subtraction model and subtracting the single merged CSG subtraction model from the CSG bone model.

20 Claims, 8 Drawing Sheets

INTERACTIVE CSG SUBTRACTION

TECHNICAL FIELD

This patent disclosure relates generally to surgical visualization and, more particularly to a system and method for modeling bone resection progress during a resection operation.

BACKGROUND

Visualization during an operation such as bone resection is important for ensuring that the required amount of resection occurs in the required locations without excess resection in any location. However, direct optical visualization is generally not possible, and effective real-time computerized visualization via 3D modeling has been difficult to implement due to computational complexity and expense. This latter problem is largely due to the complexity of the geometric modeling used to implement such systems.

Constructive Solid Geometry (CSG) rendering is a term used to describe techniques for displaying complex geometric models by combining other, usually simpler, models via mathematical operations such as the subtraction operation. For example, the result of a bone resection pass with a tool of a certain shape can be modeled as a subtraction of the tool shape from the bone shape. Previous image-space CSG implementations perform the computation for all subtracted models in consecutive steps; however, the performance of this technique degrades as the number of overlapping subtraction models increases. It is possible to improve performance during the subtraction of large number of models by computing a view-dependent subtraction sequence, so that non-overlapping models can be subtracted in the same rendering pass. However, again, the performance of using subtraction sequences depends on the depth complexity of the scene, and the performance improvement becomes negligible when the depth complexity is high.

It will be appreciated that this background description has been created by the inventors to aid the reader, and is not to be taken as a reference to prior art nor as an indication that any of the indicated problems were themselves appreciated in the art.

SUMMARY

In overview, the described system provides in one embodiment a method of transforming a cut procedure into a visual representation during resection via a cutting tool attached to an arm of a surgical robot. The method includes obtaining bone shape data for the bone to be resected and generating a CSG bone model. A CSG cutting tool model is also generated. During resection, tool position data is collected and multiple CSG subtraction models are generated based on the cutting tool model and the position data. To construct the visual representation of the resected bone, the CSG bone model and subtraction models are used to create an image space visual representation by merging the CSG subtraction models into a single CSG subtraction model and subtracting the single CSG subtraction model from the CSG bone model.

In a further embodiment, a non-transitory computer-readable medium is provided, having thereon instruction for generating a visual representation of a series of subtractions by a first object from a second object. The instructions include instructions for obtaining a shape data collection representing the shape of the second object and generating a constructive solid geometry (CSG) object model from the shape data collection. Instructions are also provided for generating a CSG primary subtraction model of the first object. Other instructions cause the collection of position data representing various positions of the first object relative to the second object and cause the generation of a plurality of CSG subtraction models based on the CSG primary subtraction model and the plurality of positions. Finally, additional instructions are included for transforming the CSG object model and the plurality of CSG subtraction models into an image space visual representation of the second object after the series of subtractions by the first object. This is accomplished by merging the plurality of CSG subtraction models into a single merged CSG subtraction model and subtracting the single merged CSG subtraction model from the CSG object model.

In a further embodiment, a surgical system is provided having a surgical robot for holding an operator-directed cutting tool during cutting of a bone and a display system for displaying a visualization of the bone during cutting. The display system includes, in addition to a display screen, a processor configured to generate a visualization of the bone during cutting for display on the display screen. The processor generates the visualization by producing a geometric bone model and a number of geometric cut models representing the cutting tool at various positions relative to the bone, combining the plurality of cut models in image space to produce a merged cut model, and subtracting the merged cut model from the bone model, yielding a resected bone image.

Further and alternative aspects and features of the disclosed principles will be appreciated from the following detailed description and the accompanying drawings, of which:

DETAILED DESCRIPTION

This disclosure relates to surgical visualization, e.g., visualizing the effect of bone resection passes during a bone resection operation such as to implant a device or structure into the bone. As noted above, constructive solid geometry is a technique that can be used to model solid objects for visualization of the objects and how they interact. For example, objects in a CSG model of a bone resection would include the bone as well as the tool, with the goal of providing accurate real-time 3D visualization of the bone resection process.

Figure 1:
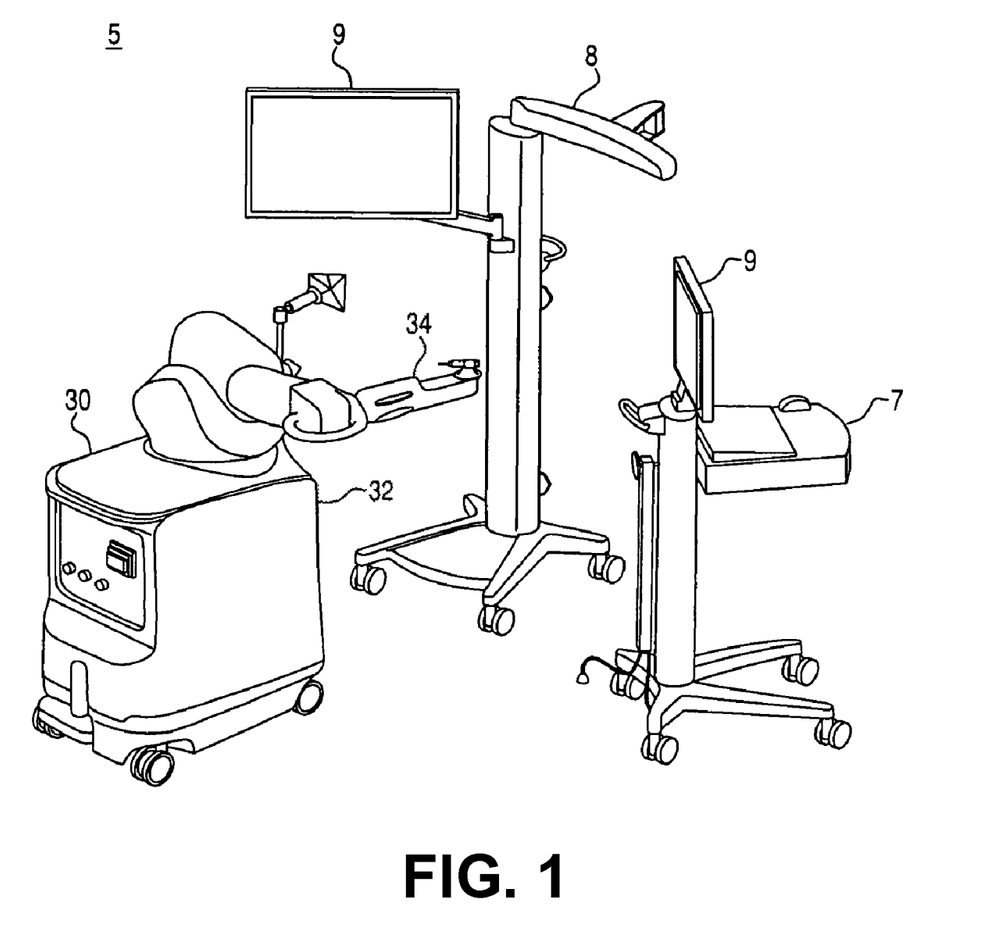
FIG. 1 is a perspective view of a surgical system usable within embodiments of the disclosed principles.

In an embodiment, the resection tool is mounted to and optionally guided by a surgical robot system. Although the precise configuration of the surgical robot system is not critical, an example of a suitable system is shown in FIG. 1. The illustrated surgical robot system 5 includes a computer assisted navigation system 7, a tracking device 8, a display device 9 (or multiple display devices 9), and a robotic arm 30.

The robotic arm 30 can be used in an interactive manner by a surgeon to perform a surgical procedure on a patient, such as a hip replacement procedure. The robotic arm 30 includes a base 32, an articulated arm 34, an optional force system (not shown), and a controller (not shown). A surgical tool is coupled to the articulated arm 34, and the surgeon manipulates the surgical tool by grasping and manually moving the articulated arm 34 and/or the surgical tool.

The force system and controller may be configured to provide control or guidance to the surgeon during manipulation of the surgical tool. In particular, the force system may be configured to provide at least some force to the surgical tool via the articulated arm 34, and the controller may be programmed, in part, to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. patent application Ser. No. 11/357,197 (Pub. No. US 2006/0142657), filed Feb. 21, 2006, and/or U.S. patent application Ser. No. 12/654,591, filed Dec. 22, 2009, each of which is hereby incorporated by reference in its entirety. In a preferred embodiment the surgical system is the RIO® Robotic Arm Interactive Orthopedic System manufactured by MAKO Surgical Corp. of Fort Lauderdale, Fla. The force system and controller may be housed within the robotic arm 30.

The tracking device 8 is configured to track the relative locations of the surgical tool (coupled to the robotic arm 34) and the patient's anatomy. The surgical tool can be tracked directly by the tracking device 8. Alternatively, the pose of the surgical tool can be determined by tracking the location of the base 32 of the robotic arm 30 and calculating the pose of the surgical tool based on joint encoder data from joints of the robotic arm 30 and a known geometric relationship between the surgical tool and the robotic arm 30. In particular, the tracking device 8 (e.g., an optical, mechanical, electromagnetic, or other known tracking system) tracks (or enables determination of) the pose (i.e., position and orientation) of the surgical tool and the patient's anatomy so the navigation system 7 is apprised of the relative relationship between the tool and the anatomy.

In operation, an operator, e.g., a surgeon, manually moves the robotic arm 30 to manipulate the surgical tool to perform a surgical task on the patient, such as bone cutting. As the surgeon manipulates the tool, the tracking device 8 tracks the location of the surgical tool and the robotic arm 30 optionally provides haptic (or force) feedback to limit the surgeon's ability to move the tool beyond a predefined virtual boundary that is registered (or mapped) to the patient's anatomy, which results in highly accurate and repeatable bone cuts. The robotic arm 30 operates in a passive manner and provides haptic feedback when the surgeon attempts to move the surgical tool beyond the virtual boundary. The haptic feedback is generated by one or more actuators (e.g., motors) in the robotic arm 30 and transmitted to the surgeon via a flexible transmission, such as a cable drive transmission. When the robotic arm 30 is not providing haptic feedback, the robotic arm 30 may be freely moveable by the surgeon and preferably includes a virtual brake that can be activated as desired by the surgeon.

During the surgical procedure, the navigation system 7 displays images related to the surgical procedure on one or both of the display devices 9. In an embodiment of the described principles, accurate visualization of the procedure is provided via a number of specific capabilities. As a first example of the visualization provided via one or both of the display devices 9 during resection, the user is able to see bone material disappear in the image when the actual cutting tool penetrates the actual bone surface. The displayed resected bone surface in this embodiment conforms to the shape of the tool across all locations where the cutting tool has been positioned during resection up to that point in time. Moreover, during the operation the user is able to stop and visually inspect the result of the resection thus far by rotating, translating, and zooming into the 3D resected virtual bone model on the display devices 9.

In a further embodiment, a color scheme is applied relative to the resected bone surface to indicate what part of the bone remains to be removed. The part of the bone that the operator still needs to resect to complete the procedure may be displayed in a different color or pattern than the rest of the bone. In addition, the process according to this embodiment may use a third color or pattern to indicate parts of the bone surface that were, but should not have been, resected.

Figure 2:
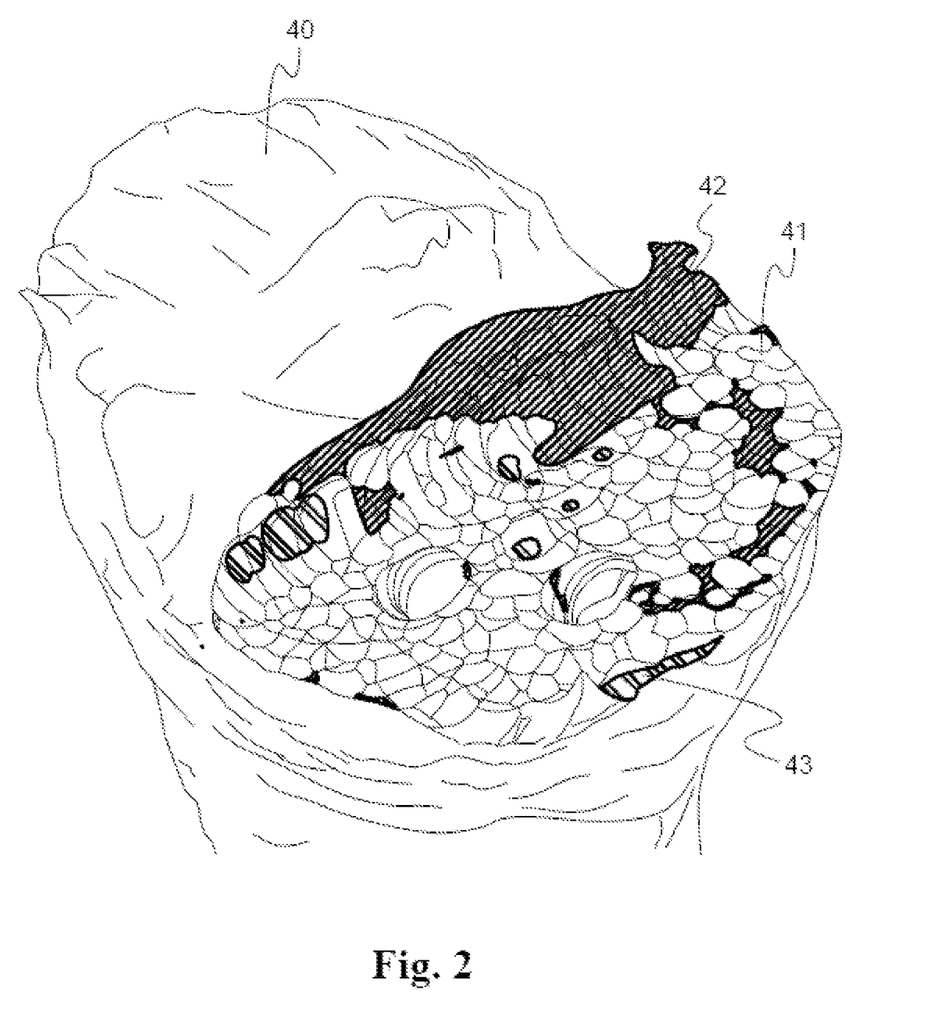
FIG. 2 is a sample perspective rendering of a resected bone showing an internal surface for matching an implant or other device.

These various techniques are visible in the schematized illustration of FIG. 2. Note that as displayed on one or both of the display devices 9, the image may be rendered in color and may appear more life-like; however, the illustrated rendering of FIG. 2 is sufficient to demonstrate the capabilities being discussed. Thus, referring to FIG. 2, the bone 40 has been resected to expose an internal surface 41 matching an implant or other object to which the resection is intended to mate.

Certain locations indicated by a first hashing such as location 42 have not yet been fully resected. As location 42 becomes fully resected, the hashing, which in an actual screen rendering may be a color such as green, disappears. Certain other locations 43, indicated by a second hashing which in an actual screen rendering may be a second color such as red, are overly resected. In these locations, the operator has removed too much material, and the surface treatment (e.g., hashing or color) notifies the operator not to resect any further in these regions. In either case, the coloring or hatching is applied via a CSG paint operation.

In order to create the necessary memory structures to display a resection procedure in the manner shown in FIG. 2, the elements of the system are modeled and manipulated via CSG in a specific manner. As such, a brief introduction to the basic concepts involved in CSG rendering will be given before turning to a more detailed discussion of the display system and technique.

As noted above, CSG refers generally to techniques for displaying complex geometric models by combining multiple other models via mathematical operations. In terms of the spatial volume represented by the models, the operations include the Boolean set operations of union, intersection and subtraction. When considering the surface boundary of the models or when the models have other properties, e.g. color or texture coordinates to indicate incomplete or excess resection, further CSG operations can be defined, such as clipping and painting.

The Boolean operation of union creates an object that combines both base objects in a way such that only the points that lay on the boundary of one object but do not reside inside the other object are external. Put another way, points that lay on the boundary of an object but are also located internal to the other object are not visible in any orientation of the combined object.

The Boolean operation of intersection creates an object where the boundary is made up of all points that are both external to one object and internal to the other object. Thus, for example, the intersection of a sphere with a cube having a side length larger than the sphere radius and an edge passing through the sphere center point is a quarter sphere.

The Boolean operation of subtraction is not commutative, and requires that one object be identified as being subtracted from the other. With this identification in place, the operation of subtraction produces a solid having a boundary that is made up of (a) all external points of the primary object that lie outside of the subtracted object and (b) all external points of the subtracted object that lie inside the primary object. Thus, using the sphere and cube from the above example, subtracting the cube from the sphere would produce an object shaped as a three-quarter sphere.

The operation of clipping is similar to the operation of subtraction, except that the points in set (b) are not included. The operation of painting does not change the shape of the primary object, but simply colors (or hashes or otherwise highlights) all external points of the primary object that lie inside the secondary object.

CSG rendering algorithms can be classified into two categories: object-space and image-space algorithms. Object-space algorithms modify the underlying representations of the models when performing the CSG operations. The representations can be either volumetric (voxelized solid) or surface (tessellated or algebraic) models. Volumetric algorithms perform per-voxel operations to compute the result of the input CSG expression and models. The resulting voxel model is displayed using either volume rendering or isosurface extraction (marching cubes) techniques. Surface algorithms use computational geometry techniques to construct a new surface model from the original models and CSG operations.

Image-space CSG rendering algorithms are based on computing the result of a CSG expression for a particular point of view on a per-pixel basis. Each pixel represents a ray cast from the viewpoint into the scene and the algorithm determines which surfaces are hit by the ray based on the given set of input models and CSG operations. Intermediate and final results of the algorithm are stored in 2D image-space buffers, which can be also considered as a data structure allocated for each pixel in the screen. Image space algorithms are well-suited for interactive applications, especially when the number and positions of the models are changing as a result of user input.

Figure 3:
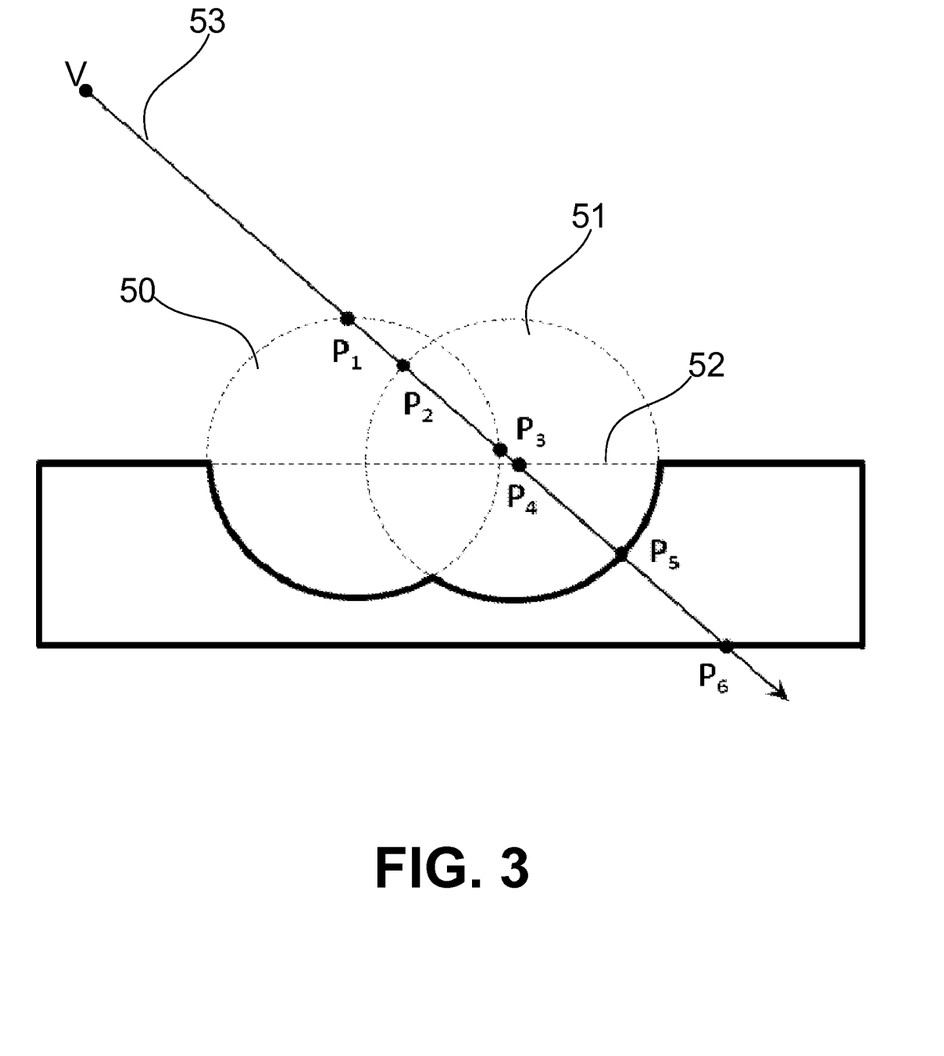
FIG. 3 is schematic drawing showing an image-space CSG rendering subtraction of two sphere models from a block model.

FIG. 3 illustrates a graphical example of implementing an image-space CSG rendering algorithm to display the result of subtracting two sphere models (sphere model 50 and sphere model 51) from a block model (block model 52). For each pixel, the algorithm finds which surfaces are intersected by the corresponding viewing ray 53. The intersections $P_1$, $P_2$, $P_3$, $P_4$, $P_5$, and $P_6$ are computed in sorted order based on their distance from the viewpoint V. The algorithm also determines if the viewing ray 53 enters or exits a particular model at the intersection locations.

In this example, the viewing ray 53 enters sphere model 50 at point $P_1$ and exits the model at point $P_3$. Similarly, the viewing ray 53 enters sphere model 51 at point $P_2$ and exits the model at point $P_5$. Finally, the ray enters block model 52 at point $P_4$ and exits the model at point $P_6$. The solution is found at the closest intersection point that is inside block model 52 and is outside both sphere models 50, 51. For this example, the displayed surface is located at point $P_5$, where the ray (1) exits sphere model 51, (2) is already outside sphere model 50, and (3) is still inside block model 52.

An exemplary way to find all relevant surfaces in a scene in front-to-back order from a viewpoint is to successively draw the surfaces using a multi-pass rendering algorithm. Although this discussion will refer to depth peeling by way of example, it will be appreciated that other techniques may instead be used at this stage to generate a sorted list of per-pixel information. For example, the known A-buffer technique is a hidden surface removal method which accounts for arbitrary overlapping edges in a pixel. In the A-buffer approach, each pixel is represented by a variable-length packet describing all potentially visible surfaces for a given pixel. The visibility data is composited to describe all of the surfaces contributing to each pixel, in order to compute the pixel's final appearance. Similarly, the k-buffer approach, which is a generalization of the traditional Z-buffer approach, uses framebuffer memory as a read-modify-write pool of entries manipulated in accordance with defined k-buffer operations. The k-buffer is generally used either to accumulate fragments for a post-processing pass or as a fragment stream processor and programmable blender.

At any rate, although alternative techniques may be suitable, depth peeling is generally less computationally complex and does not require sophisticated image processing hardware as do some of the alternative techniques such as the A-buffer and k-buffer techniques. Depth peeling uses two depth tests to find the closest surface behind a given reference surface. By iteratively setting the reference surface to the surface found in the previous pass (hence the term "peeling"), one can draw all surfaces in the scene in front to back order from the viewpoint. The required number of depth peeling iterations depends on the depth complexity of the scene, and it will be appreciated that any overlapping surfaces that result in depth collisions can be accommodated by comparing their model or rendering primitive IDs.

Turning now to CSG visualization of bone resection, a CSG expression is formulated to capture the requirements for the implementation. Each model in the scene has an associated type as follows that defines how the model is used:

Bone: A surface model of the bone before resection obtained from the segmentation of input data such as from an input CT scan data set. The model is a watertight closed model.

Implant: A surface model representing the volume of bone that needs to be removed. The model may be created based on a simplified version of the actual implant model. The model is a watertight closed model.

Margin: A surface model offset from the Implant type model in the outward direction, e.g., by about 1 mm, defining a safety zone around the implant that can still be resected without serious consequences. The model is a watertight closed model.

Cut: A simplified surface model of the cutting tool tip that is in contact with the bone during resection. The model is a watertight closed convex model.

Trim: A surface model representing the volume of bone that needs to be removed. A Trim type model can be used before resection to show what the bone would look like after resection. The model is a watertight closed model.

In the context of these models, the following CSG operations are defined for the visualization of the bone resection process:

Subtraction: $A \ominus B$ is defined as the volume of model A outside the volume of model B carrying the properties of model A. The surface of model B inside the volume of model A becomes an internal trimmed surface of model A. The surface of model A outside the volume of model B remains an original boundary surface of model A. Different visual properties can be applied to the original boundary and trimmed internal surfaces of a model.

Merging: A⊕B is defined as the volume of model A outside the volume of model B carrying the properties of model A and the volume of model B carrying the properties of model B. Only the surface of model A outside the volume of model B and the surface of model B outside the volume of model A are kept as original boundary surfaces after the merge.

Painting: A ⊙ B is defined as the volume of model A outside the volume of model B carrying the properties of model A and the volume of model A inside the volume of model B carrying the properties of model B. Only the original boundary surface of model A is kept with properties applied according to the properties of the corresponding volumes.

In view of the above-defined models and operations, the bone resection visualization produces an image of a surface model that represents the following CSG expression:

$$(Bone \otimes Margin \otimes Implant) \ominus Trim \ominus (cut1 \oplus Cut2 \oplus \ldots \oplus CutN).$$

Figure 4:
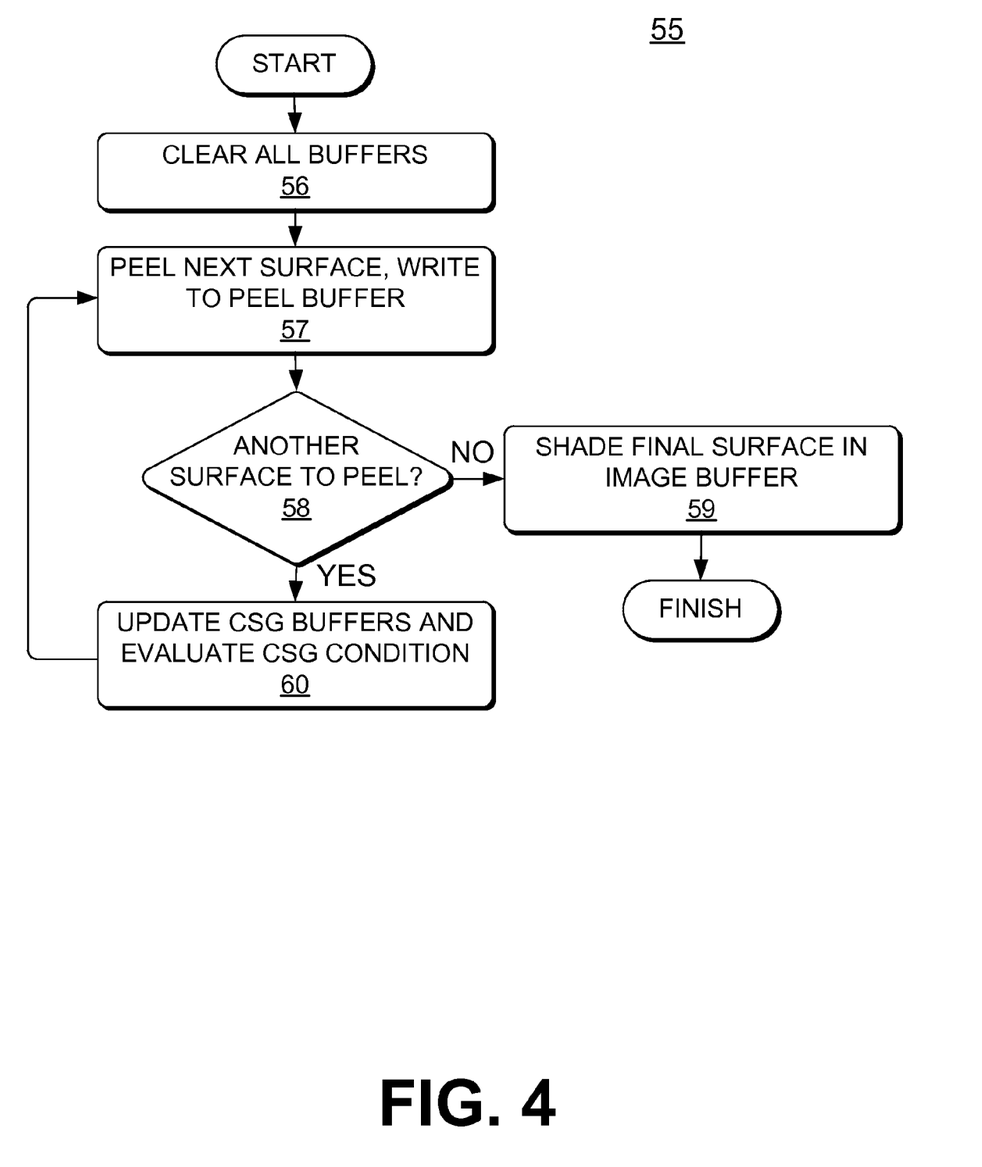
FIG. 4 is a schematic view of a hardware system for implementing a process of CSG subtraction according to an embodiment.
Figure 5:
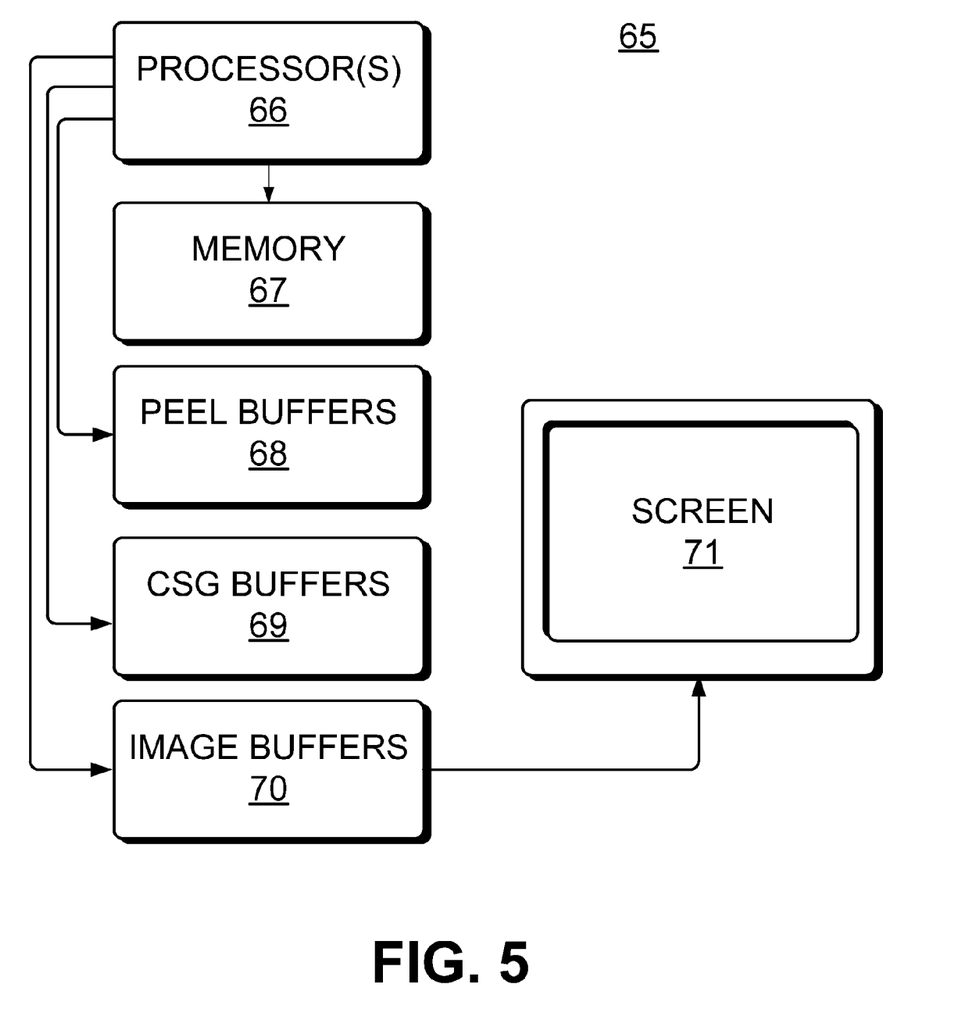
FIG. 5 is a flow chart of a process for implementing a process of CSG subtraction according to an embodiment.

In this context, the flow and components of the described depth peeling algorithm are shown in the process 55 of FIG. 4 in conjunction with the architectural diagram of FIG. 5 showing a simplified hardware system 65 for implementing the illustrated process. Referring to FIG. 5, the described process 55 is implemented via one or more processors 66 utilizing memory 67 which may includes nonvolatile memory and may also include volatile memory as needed or desired in a given implementation. The process steps discussed herein are executed by the processor(s) 66 via the computer execution of computer-readable instructions (e.g., code, programs, etc.) read from a nontransitory memory such as memory 67 and/or other memory means such as optical or magnetic disc memory, flash drives, and so on. Any of the memory structures may also store parameters or other data used by the processor(s) 66 in executing the process 55.

The processor(s) 66 writes to three sets of image-space buffers for storing information during the depth peeling and shading steps. These buffers include one or more peel buffers 68, one or more CSG buffers 69, and one or more image buffers 70. Initially at stage 56, the processor(s) 66 clears all buffers.

At stage 57, the next layer in the model data is peeled and the processor(s) 66 populates the peel buffers 68 with the depth value, the surface normal vector ("surface normal"), the model type ID, the material ID, and the front/back facing surface flag for each pixel on the screen. The model type ID is a numerical ID assigned to each possible model type in the scene. For the bone resection application, the model types distinguish between Bone, Implant, Margin, Cut, and Trim models. The material ID is a numerical ID assigned to each color and transparency combination used for the models in the scene and is used during the shading step, i.e., to show that resection in a particular location should continue, is complete, or has already gone too deep as discussed above.

The process 55 determines at stage 58 whether the layer just peeled is the last. If it is determined that the layer was the last, then the process 55 proceeds to stage 59, wherein the final surface in the image buffers 70 is shaded. If instead is it determined at stage 58 that the layer just peeled is not the last, then the process 55 flows to stage 60 to update the CSG buffers 69 and evaluate the CSG condition indicated by the data in the CSG buffers 69. From stage 60, the process 55 returns to stage 57 to peel another layer.

As the process 55 proceeds, the CSG buffers 69 will be updated with per-pixel counters for each model type ID, the material ID for the last peeled surface, and the final normal vectors and depth values for those pixels that the CSG condition marked complete. During the CSG update step, the model type counters are updated based on the model type ID and front/back information of the incoming pixel from the peel buffers. The counter for a given model type ID is incremented for front surface pixels and decremented for back surface pixels, and thus encodes when the corresponding viewing ray enters or exits a model of a given type. After the counters are updated, the following condition is evaluated to determine if the pixel can be marked completed or not:

completed := outsideCutType AND (on Bone OR in Bone)
where:
outsideCutType := counter[CUT]=0 AND counter[TRIM]= 0
on Bone := frontFacing AND modelType=BONE
in Bone := backFacing AND counter[BONE]>0 AND (modelType=CUT OR modelType=TRIM).

Once a pixel is marked complete, the corresponding depth, material ID, and normal values are stored in the CSG buffers 69 for the subsequent shading step. The shading step 59 discussed above reads these values from the CSG buffers 69 and writes the final shaded pixel color values to the image buffers 70. The contents of the image buffers 70 are then written to the display screen 71 at a suitable refresh interval, e.g., ten times per second.

The described depth peeling process 55 produces the correct result for any combination of CSG operations for any set of watertight closed input models. Since rendering performance depends on the depth complexity of the scene however, the input data may be preprocessed to allow more fluid interactive display of a large number of overlapping models. In the context of bone resection visualization, one of the most computationally expensive processes is the subtraction of hundreds or thousands of overlapping Cut type models due to the depth complexity of the scene.

Thus, in an embodiment, the depth complexity of the scene is first reduced by converting the set of "Cut" type models to an imaged-based representation referred to herein as a layered depth image (LDI). An LDI stores the depth values for all model surfaces located under a pixel for a particular view. The union of a set of such models can be represented with a simplified LDI that stores only the boundary of the union.

Figure 6:
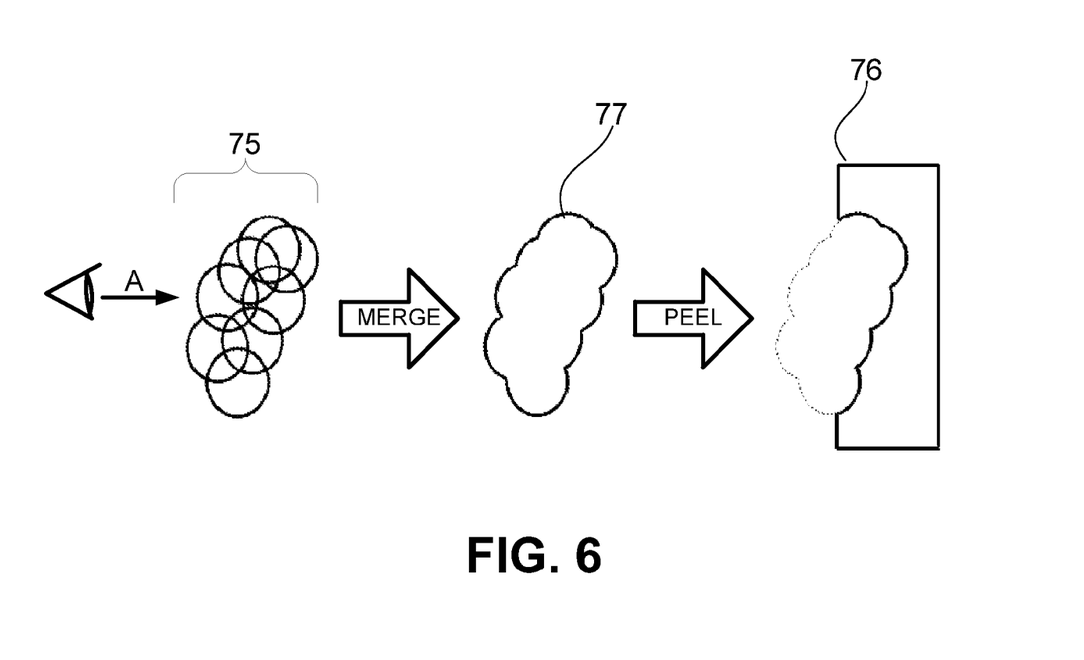
FIG. 6 is a series of simplified image representations showing an example of a process for creating a layered depth image in accordance with an embodiment.

The described process for creating an LDI is shown graphically in FIG. 6. The model environment in the illustrated example includes a set of subtraction models 75 (e.g., cutting tool pass models) and a target object model 76, which in the illustrated example is a block, but which in application may be a bone or other structure. Initially, the subtraction models 75 are converted to an image-based representation 77 that signifies the union of the models 75. Next, the image-based representation 77 is used in the depth peeling algorithm to compute the subtracted result, e.g., the target object model 76 less the aggregate of the subtraction models. The image-based format reduces the depth complexity of the scene by eliminating overlapping regions and results in a significant speedup over subtracting individual models.

Figure 7A:
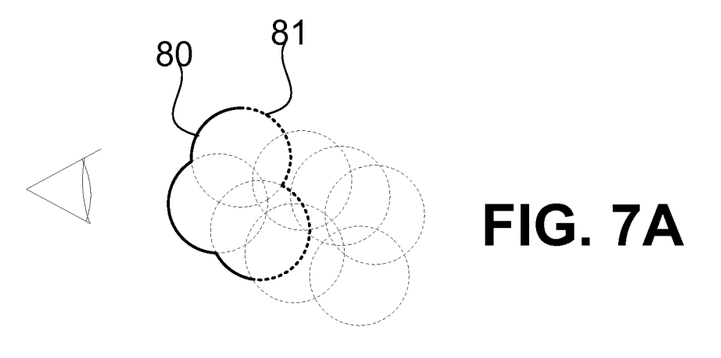
FIGS. 7A-7D are a series of images showing an example of layer peeling in accordance with the described principles.

Referring to the step of merging the individual subtraction models 75 into an image-based representation 77 signifying the union of the models 75, the flow illustration of FIGS. 7A-7D demonstrates this process graphically in greater detail. As shown in FIG. 7A, the models are first grouped into model layers based on the distance of their origin from the viewpoint. The closest model layer is rendered to obtain the front 80 and back 81 facing depth values and normal vectors representing the union of the layer. The resulting depth values and normal vectors are merged into a separate buffer that stores the LDI.

Figure 7B:
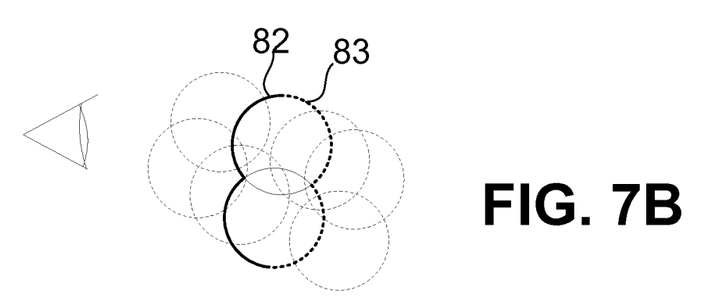
Figure 7C:
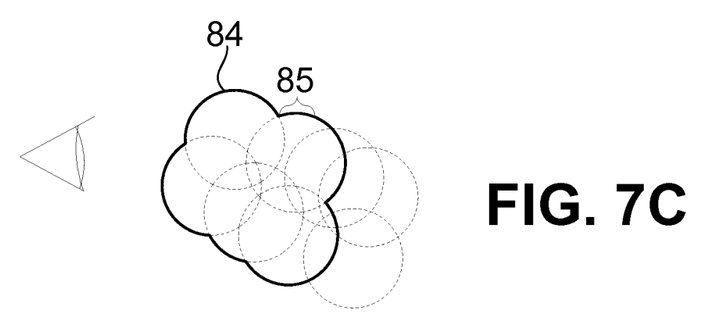

The second closest layer is then rendered as in FIG. 7B to obtain its corresponding front 82 and back 83 facing depth values and normal vectors. As shown in FIG. 7C, the depth values and normal vectors are merged into the LDI buffer, which now represents the union 84 of both model layers after the merge. If a front facing portion of the union 84 is obscured, i.e., if the front facing depth value of the incoming model layer is larger than the back facing depth value in the LDI buffer layer, a new LDI buffer layer is created, as illustrated by region 85.

Figure 7D:
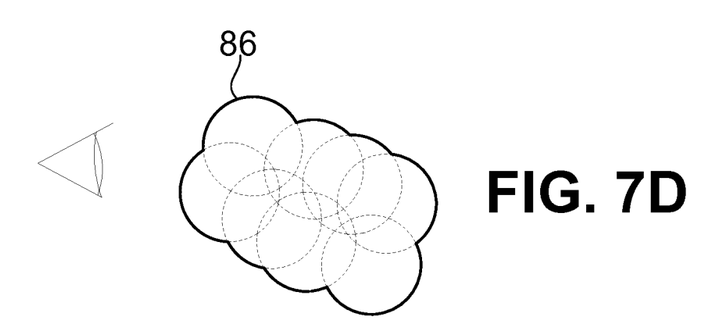

The foregoing process is then repeated between the union 84 and the next layer rearward to derive a new union. The final resulting LDI 86 is shown in FIG. 7D. For this example, two LDI buffer layers are sufficient to represent the scene; in practice more layers may be needed. In general, for a set of subtraction objects with depth complexity of N, there will be a need for N/2 LDI buffer layers. For the bone resection application, only the closest layer intersecting the bone is relevant, because layers outside the bone or behind the closest intersecting layer will have no impact on the final visualization. The closest intersecting layer can be found by including the bone model in the LDI generation algorithm.

Figure 8:
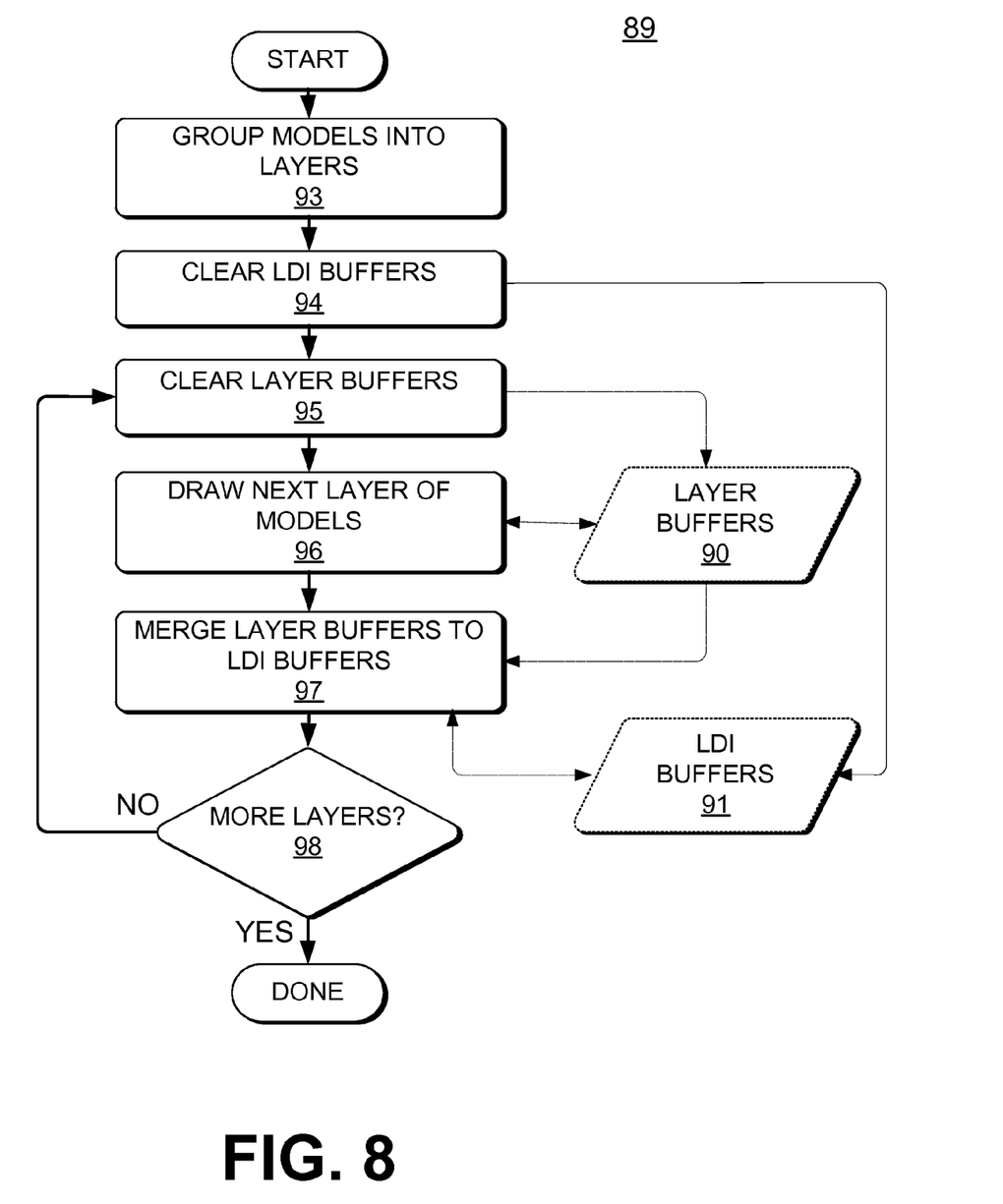
FIG. 8 is a flow chart illustrating a process for LDI generation in accordance with one embodiment.

The simplified LDI is then used in the depth peeling algorithm to compute the subtraction of a large number of models in a single pass, which results in a significant speedup over subtracting individual models in multiple passes. The process 89 for LDI generation in accordance with one embodiment is shown in FIG. 8. In the figure, the solid lines represent process flow, while the dashed lines represent data and/or control information flow.

The process 89 employs two sets of image-space buffers for storing per-pixel information during the rendering and merging steps. The layer buffers 90 store the front and back facing depth values and surface normals for each pixel on the screen. The LDI buffers 91 contain a fixed number of LDI layers, each storing the front and back facing depth values and surface normals for the layer.

At stage 93, the process 89 begins by grouping the models into layers. The LDI buffers 91 are cleared at stage 94 and the layer buffers 90 are cleared at stage 95. Having thus initialized the buffers 90, 91, the process flows to stage 96, wherein the next layer (or first layer during the first iteration after initialization) is drawn into the layer buffers 90. The depth values and normal vectors stored in the layer buffers 90 are then merged into the LDI buffers 91 at stage 97, such that the LDI buffers 91 now represent the union of both model layers after the merge.

At stage 98, the process 89 determines whether there are further model layers to be processed. If there are additional layers to be processed, the system returns to stage 95 to clear the layer buffers 90, and then proceeds with the drawing of the next layer as described above. Once there are no further layers to be processed, then the contents of the LDI buffer represent the final result of merging subtraction models, and can subsequently be used in the image generation process.

While the CSG technique is very useful for visualization, it may also be used to implement haptic feedback through the surgical robot 30. For example, locations in the bone model that are designated as being red (i.e., as being over-resected) may not be allowed, with the robot providing feedback biasing the tool from entering such regions. Similarly, tool movement within bone regions that are uncolored (no further resection required but margin not yet breached) or green (continue to resect) may be unrestricted. Alternatively, three different degrees of feedback, from no feedback to strong resistance, may be used to distinguish between all three types of regions.

Although the foregoing discussion exemplifies the described principles via a discussion of bone resection, it will be appreciated that the described principles are more widely applicable. For example, the described principles are applicable to any type of operation wherein multiple instances of a tool or other instrument model are to be subtracted from a bone or other biological structure model.

It will be appreciated that the foregoing description provides useful examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for the features of interest, but not to exclude such from the scope of the disclosure entirely unless otherwise specifically indicated.

I claim:

1. A method of transforming a cut procedure into a visual representation of a bone cut during resection via a cutting tool, wherein the cutting tool is attached to an arm of a surgical robot, the method comprising:
   obtaining a bone shape data collection representing a shape of a bone to be resected and generating a bone model from the bone shape data collection;
   generating a cutting tool model of the cutting tool;
   collecting tool position data representing a plurality of positions of the cutting tool relative to the bone during resection of the bone and generating a plurality of subtraction models based on the cutting tool model and the plurality of positions; and
   transforming the bone model and the plurality of subtraction models into an image space visual representation of the bone cut by merging the subtraction models into a single subtraction model and subtracting the single subtraction model from the bone model, the single subtraction model representing the resection.

2. The method of transforming a cut procedure into a visual representation of a bone cut during resection via a cutting tool according to claim 1, wherein obtaining a bone shape data collection comprises receiving CT scan data.

3. The method of transforming a cut procedure into a visual representation of a bone cut during resection via a cutting tool according to claim 1, wherein collecting tool position data includes receiving a plurality of position indications from the surgical robot and selecting a subset of position indications, each of which represents a position that spatially varies from a temporally adjacent position by more than a predetermined distance.

4. The method of transforming a cut procedure into a visual representation of a bone cut during resection via a cutting tool according to claim 1, wherein generating a plurality of subtraction models based on the cutting tool model and the plurality of positions includes creating a subtraction model at each of the plurality of positions.

5. The method of transforming a cut procedure into a visual representation of a bone cut during resection via a cutting tool according to claim 4, wherein merging the subtraction models into a single subtraction model comprises depth peeling the subtraction models to create the single subtraction model.

6. The method of transforming a cut procedure into a visual representation of a bone cut during resection via a cutting tool according to claim 5, wherein depth peeling the subtraction models comprises:
grouping the subtraction models into a plurality of image layers, each layer comprising a collection of depth values and normal vectors; and
sequentially updating a first buffer by sequentially drawing the depth values and normal vectors of each image layer into a second buffer starting at a closest layer of the visual representation to a view point, and, after each such drawing, merging the depth values and normal vectors in the second buffer into the first buffer, and clearing the second buffer.

7. A non-transitory computer-readable medium having thereon computer-executable instruction for generating a visual representation of a series of subtractions by a cutting tool from a bone, the series of subtractions comprising a series of cuts from the bone by the cutting tool during resection of a bone cut, the instructions comprising:
instructions for obtaining a shape data collection representing a shape of the bone and generating an object model from the shape data collection;
instructions for generating a primary subtraction model of the cutting tool;
instructions for collecting position data representing a plurality of positions of the cutting tool relative to the bone and generating a plurality of subtraction models based on the primary subtraction model and the plurality of positions; and
instructions for transforming the object model and the plurality of subtraction models into an image space visual representation of the bone after the series of subtractions by the cutting tool by merging the plurality of subtraction models into a single merged subtraction model and subtracting the single merged subtraction model from the object model, the single merged subtraction model representing the resection.

8. The non-transitory computer-readable medium according to claim 7, wherein the instructions for obtaining a shape data collection comprise instructions for receiving CT scan data of the bone.

9. The non-transitory computer-readable medium according to claim 7, wherein the instructions for collecting position data representing a plurality of positions of the cutting tool relative to the bone include instructions for receiving a plurality of position indications from a surgical robot for the cutting tool and selecting a subset of position indications, each of which represents a position that spatially varies from a temporally adjacent position by more than a predetermined distance.

10. The non-transitory computer-readable medium according to claim 7, wherein the instructions for generating a plurality of subtraction models based on the primary subtraction model and the plurality of positions include instructions for creating a subtraction model at each of the plurality of positions.

11. The non-transitory computer-readable medium according to claim 9, wherein the instructions for merging the subtraction models into a single merged subtraction model comprise instructions for depth peeling the plurality of subtraction models to create the single merged subtraction model.

12. The non-transitory computer-readable medium according to claim 11, wherein the instructions for depth peeling the subtraction models comprise:
instructions for grouping the subtraction models into a plurality of image layers, each layer comprising a collection of depth values and normal vectors; and
instructions for sequentially updating a first buffer by sequentially drawing the depth values and normal vectors of each image layer into a second buffer starting at a closest layer of the visual representation to a view point, and after each such drawing, merging the depth values and normal vectors in the second buffer into the first buffer, and clearing the second buffer.

13. A surgical system comprising:
a surgical robot for holding an operator-directed cutting tool during cutting of a bone; and
a display system for displaying a visualization of the bone during cutting, the display system comprising:
a display screen; and
a processor configured to generate a visualization of the bone during cutting for display on the display screen by executing instructions including instructions to produce a geometric bone model of the bone and a plurality of geometric cut models representing the cutting tool at a corresponding plurality of positions relative to the bone, to combine the plurality of cut models in image space to produce a merged cut model, the merged cut model representing a resection, and to subtract the merged cut model from the bone model, yielding a resected bone image.

14. The surgical system in accordance with claim 13, wherein the resected bone image identifies portions of the bone that have not yet been cut to a predetermined point.

15. The surgical system in accordance with claim 14, wherein the resected bone image further identifies portions of the bone that have been cut past the predetermined point.

16. The surgical system in accordance with claim 13, wherein the display system further comprises a plurality of image space buffers used by the processor to generate the resected bone image.

17. The surgical system in accordance with claim 13, wherein the surgical robot for holding an operator-directed cutting tool is configured to provide physical resistance via the cutting tool with respect to movements of the cutting tool beyond a predefined boundary.

18. The surgical system in accordance with claim 17, wherein the predefined boundary corresponds to a shape of a bone implant.

19. The surgical system in accordance with claim 13, wherein the instructions to produce a geometric bone model include instructions to generate the geometric bone model based on received CT scan data.

20. The surgical system in accordance with claim 13, wherein the instructions to combine the plurality of cut models in image space to produce a merged cut model include instructions to group the cut models into layers and sequentially combine the layers.

* * * * *